United States Patent [19]

Lindley

[11] Patent Number: 5,118,860

[45] Date of Patent: Jun. 2, 1992

[54] BF3 CATALYZED ACYLATION OF AROMATIC COMPOUNDS

[75] Inventor: Charlet R. Lindley, Portland, Tex.

[73] Assignee: Hoechst Celanese Corporation, Somerville, N.J.

[21] Appl. No.: 619,157

[22] Filed: Nov. 27, 1990

[51] Int. Cl.$^5$ .............................................. C07L 45/45
[52] U.S. Cl. .................................. 568/323; 568/319; 568/322
[58] Field of Search ........................ 568/319, 322, 328

[56] References Cited

U.S. PATENT DOCUMENTS

| | | | |
|---|---|---|---|
| 2,245,721 | 6/1941 | Ross et al. | 260/476 |
| 3,234,286 | 2/1966 | Lawrence | 568/319 |
| 4,007,125 | 2/1977 | Mott | 568/319 |
| 4,454,350 | 6/1984 | Desbois | 568/319 |
| 4,474,990 | 10/1984 | Jansons | 568/319 |
| 4,607,125 | 8/1986 | Mott | 568/319 |
| 4,777,300 | 10/1988 | Colquhoun et al. | 568/319 |
| 4,982,005 | 1/1991 | Neumann et al. | 568/319 |

FOREIGN PATENT DOCUMENTS

| | | | |
|---|---|---|---|
| 202403 | 11/1986 | European Pat. Off. | 568/319 |
| 6197240 | 5/1986 | Japan | 568/319 |
| 2102420 | 2/1983 | United Kingdom | 568/319 |

OTHER PUBLICATIONS

Takura, Chem. Abst., vol. 76, #45254w (1972).
Chem. Abs., 86-286372/44 EP-199661 "Preparation of diacyl: biphenyl cmpds.", Apr. 16, 1985.

Primary Examiner—James H. Reamer
Attorney, Agent, or Firm—Shirley Church; Michael Tulley

[57] ABSTRACT

In accordance with the present invention, aromatic ketones are prepared by the acylation of aromatic reactants using boron trifluoride as a catalyst and in a solvent medium comprising anhydrous liquid sulfur dioxide. The acylation proceeds in accordance with the equation I:

$$\text{I. } X_n \text{-Ar-H} + \text{RCY} \xrightarrow[\text{SO}_2]{\text{BF}_3} X_n \text{-Ar-C}=\text{O} + \text{HY}$$

(with the acyl group RCY containing C=O, and product containing R–C=O)

wherein n ranges from 5 to 9, Ar is phenylene and n is 5, naphthalene and n is 7, or a bis phenylene radical having the structure:

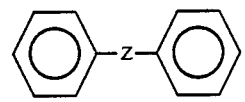

and n is 9; wherein Z is selected from the group consisting of a covalent carbon to carbon bond, O, S, SO$_2$, C=O and C$_1$ to C$_3$ alkylene or alkylidene, X is selected from the group consisting of H, OH, halogen, C$_1$ to C$_6$ alkyl C$_1$ to C$_6$ alkoxy and combinations thereof, R is an alkyl group containing from 1 to about 16 carbon atoms and Y is selected from the group consisting of hydroxy, acyloxy and halogen.

The acylation process of this invention gives rise to aromatic ketones which are highly selectively acylated at the activated ring carbon and also yields a high ratio of conversion of the aromatic starting material.

The process also provides a faster rate of reaction than analogous processes and affords the opportunity to recover large quantities of the BF$_3$ catalyst as well as the SO$_2$ solvent for recycle, thus offering improved economy and efficiencies.

11 Claims, No Drawings

BF3 CATALYZED ACYLATION OF AROMATIC COMPOUNDS

BACKGROUND OF THE INVENTION

1. Field of the Invention

This invention relates to an improved process for the acylation of aromatic compounds utilizing boron trifluoride as a catalyst and liquid sulfur dioxide as a solvent.

2. Description of Related Art

Aromatic ketones are valuable intermediates useful in the production of pharmaceutical compounds, cosmetics and in other applications.

For example, U.S. Pat. No. 4,607,125 discloses that hydroxy aromatic ketones, such as 4-hydroxyacetophenone, are useful in the production of N-acyl-p-aminophenol, better known as acetaminophen which has wide use as an analgesic. Acylation is accomplished by reacting phenol with an acylating agent such as acetic anhydride in the presence of a Friedel-Crafts type catalyst such as aluminum chloride, hydrogen fluoride (HF) or boron trifluoride ($BF_3$). HF is preferred because it also serves as a solvent medium for the reaction.

U.K. Patent publication 2102420A teaches the preparation of aromatic diaryl ketones by reacting a substituted benzene with an aromatic acyl compound in the presence of a mixture of a Lewis acid which may include $BF_3$ and a strong acid which may include HF. The reaction medium may also include a polar solvent such as sulfur dioxide, tetramethylene sulfone, nitrobenzene and similar materials.

U.S. Pat. No. 4,454,350 discloses the preparation of p-haloacetophenones which are useful as intermediates in the preparation of pharmaceutical compounds and herbicides wherein starting materials such as fluorobenzene are reacted with an acylating agent such as acetic anhydride or acetyl chloride in a mixed system comprising HF as a solvent and $BF_3$ as a catalyst.

European Patent Publication EP-199661-A teaches the acylation of biphenyl to produce 4-acetyl biphenyl or 4,4,-diacetyl biphenyl using an acetylating compound such as acetic anhydride and using HF, or a mixture of HF and $CH_2Cl_2$ as solvents, and $BF_3$ as the reaction catalyst.

U.S. Pat. No. 4,474,990 discloses a similar process for the preparation of p-phenoxybenzoyl compounds, which are useful in the production of polyetherketone resins, by acylation of diphenyl ether using an acylating compound such as acetic anhydride and HF as a catalyst and diluent. The reference indicates on the top of column 3 that the reaction media may also include an optional diluent such as alkanes, haloalkanes, sulfur dioxide and similar materials.

Ibuprofen [2-(4'-isobutylphenyl)propionic acid] is a well-known nonsteroidal anti-inflammatory pharmaceutical which has been converted from ethical, i.e., prescription, to over-the-counter status. It is generally prepared by the catalytic acetylation of isobutyl benzene (IBB) with a suitable acetylation compound such as acetic anhydride to form 4-isobutylacetophenone (IBAP). The reduction (catalytic hydrogenation) of IBAP leads to 1-(4'-isobutylphenyl) ethanol (IBPE); carbonylation of IBPE yields Ibuprofen.

The preparation of 4-isobutylacetophenone from isobutylbenzene is known in the art. For example, Braddely et al., Journal of the American Chemical Society, 4943–4945 (1956), discloses on p. 4945 the preparation of 4-isobutylacetophenone by the Friedel-Crafts acetylation of isobutylbenzene with acetyl chloride using aluminum chloride as a catalyst.

In addition, Japanese Patent Publication no. 60 [1985]-188343 discloses the preparation of 4-isobutylacetophenone by the acetylation of isobutylbenzene using acetyl fluoride as an acetylating agent, which is prepared by reacting acetic anhydride with HF as a catalyst, or a combination of HF and $BF_3$ as catalysts.

Commonly assigned copending application Docket Number N-7043C discloses a process for acetylating isobutylbenzene using an appropriate acetylating agent such as acetic anhydride and in the presence of HF which serves as a catalyst and solvent.

While all of the above and other acylation processes are effective to varying degrees, they suffer certain deficiencies, particularly when scaled up for commercial production. For example, conventional Friedel Crafts catalysts such as aluminum chloride either can not be recycled or are recycled with difficulty from the reaction mass. In addition, HF is a highly protic solvent and the separation of HF from an HF/$BF_3$/aromatic ketone reaction product must be accomplished rapidly in order to avoid decomposition of the aromatic ketone reaction product. This would require the utilization of a reactor distillation column to effect this separation. Yet a third factor is the percent conversion of the aromatic starting material to the desired ketone and the selectivity of the process for producing the desired ketone as compared with its isomers. Conversion and selectivity are largely a function of the specific catalyst and the solvent employed in the process. For example, in the commercial process for preparing 4-isobutylacetophenone from isobutylbenzene using acetic anhydride as an acetylating agent and HF as a catalyst, the reaction generally proceeds with less than 90% conversion of the isobutylbenzene starting material and less than 85% selectivity toward production of the desired 4-isomer vs. other isomers such as the 3-isomer or 3,4-isomer combination.

Such drawbacks result in production inefficiencies due to the requirement for additional separation and/or purification steps in the production process, as well as equipment for accomplishing these steps, and lower yields of the desired product.

Acylation of aromatic compounds using an aluminum halide catalyst and a solvent medium other than HF have been described in the prior art. For example, U.S. Pat. No. 2,245,721 discloses the acylation of aromatic compounds by reaction with carboxylic acid halides or anhydrides in the presence of an aluminum halide catalyst and liquid sulfur dioxide as a solvent. Although the patent describes numerous advantages which inure as the result of using sulfur dioxide in the process, the yield of reaction product is extremely low, e.g., a 45% yield of acetophenone from benzene and acetyl chloride using an aluminum chloride catalyst as indicated in Example 3 of the patent. Also, as pointed out above, the aluminum chloride catalyst can not be recycled for further use as is desirable in a commercial scale process.

Accordingly, it is an object of this invention to provide an efficient and economical process for preparing aromatic ketones.

Another object of this invention is to provide a process for acylating aromatic compounds without the need to use highly protonic solvents.

Another object is to provide a process for preparing 4-isobutylacetophenone wherein a high conversion of the isobutylbenzene starting material is realized.

Yet another object is to provide an acetylation process which is highly selective towards the production of 4-isobutylacetophenone in contrast to its related isomers.

SUMMARY OF THE INVENTION

In accordance with the present invention, aromatic ketones are prepared by the acylation of aromatic reactants using boron trifluoride as a catalyst and in a solvent medium comprising anhydrous liquid sulfur dioxide. The acylation proceeds in accordance with the equation I:

I. $X_n \mathbin{+} Ar \mathbin{+} H + RCY \xrightarrow[SO_2]{BF_3} X_n \mathbin{+} Ar \mathbin{+} C=O + HY$ 

wherein n ranges from 5 to 9, Ar is phenylene and n is 5, naphthalene and n is 7, or a bis phenylene radical having the structure:

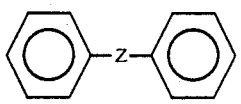

and n is 9; wherein Z is selected from the group consisting of a covalent carbon to carbon bond, O, S, $SO_2$, C=O and $C_1$ to $C_3$ alkylene or alkylidene, X is selected from the group consisting of H, OH, halogen, $C_1$ to $C_6$ alkyl $C_1$ to $C_6$ alkoxy and combinations thereof, R is an alkyl group containing from 1 to about 16 carbon atoms and Y is selected from the group consisting of hydroxy, acyloxy and halogen.

The quantity of reactants, catalyst and anhydrous $SO_2$ employed in the process per mole of aromatic starting material may generally range from as little as about 0.5 mole acylation agent (where it is used in the anhydride form) up to about 4 moles, from about 1 to about 15 moles of $BF_3$, and from about 5 to 75 moles of anhydrous $SO_2$. The reaction may be conducted at pressures ranging from about 2.5 to 500 psig and at temperatures within the range of from about $-60°$ C. to about $+50°$ C.

The acylation process of this invention gives rise to aromatic ketones which are highly selectively acylated at the activated ring carbon and also yields a high ratio of conversion of the aromatic starting material. The process also provides a faster rate of reaction than analogous processes and affords the opportunity to recover large quantities of the $BF_3$ catalyst as well as the $SO_2$ solvent for recycle, thus offering improved economy and efficiencies.

DETAILED DESCRIPTION OF THE INVENTION

Aromatic starting materials within the scope of the formula $X_n[Ar-H$ in equation I above which may be employed in the process of this invention preferably include compounds wherein X is selected from the group consisting of H, OH, and branched or straight chain $C_1$ to $C_6$ alkyl. Preferred compounds wherein Ar is a monocyclic phenylene radical include benzene, phenol, and branched or straight chain monoalkyl aromatics wherein at least one X is more preferably a $C_1$ to $C_4$ hydrocarbon, such as toluene, isopropylbenzene and isobutylbenzene. Preferred compounds wherein Ar is a bis phenylene radical are those wherein the para (or 4) position on the ring is the preferred position for a non-hydrogen X, and where Z is selected from the group consisting of a covalent carbon to carbon bond, oxygen, methyl, and sulfur. Suitable compounds include biphenyl, diphenyl ether, diphenyl methane and diphenyl sulfide. Suitable aromatics based on a naphthylene nucleus include naphthalene, 2-methyl naphthalene and 2-methoxy naphthalene.

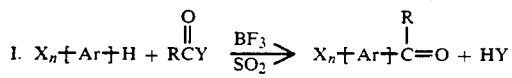

Acylating agents within the scope of the formula set forth in equation I above are preferably those wherein R is an alkyl group containing 1 to 4 carbon atoms and Y is selected from the group consisting of hydroxy, acyloxy, chloride, fluoride, or bromide. More preferred species include acids or anhydrides such as acetic, propionic and n-butyric acids or anhydrides as well as the corresponding acid halides. Where the acylation reaction is acetylation, then acetylating agents which may be employed include acetic acid, acetic anhydride, acetyl fluoride, acetyl chloride, acetyl bromide and ketene which results from the abstraction of HY from the foregoing acetylating agents prior to the acetylation reaction. Acetic anhydride is the preferred acetylation agent.

The more preferred molar ratio of acylating agent used per mole of aromatic starting material (within the 0.5 to 4 mole range set forth above) is from about 1 to about 3 moles, most preferably from about 1.1 to about 2 moles.

The boron trifluoride catalyst is more preferably the sole catalyst employed in the process and thus the catalyst consists of $BF_3$. It may be used in its normal gaseous state or may be introduced into the reactor in the form of the liquid $BF_3$-etherate or $BF_3$-hydrate complex which will decompose in anhydrous $SO_2$ to form the $BF_3.SO_2$ complex in-situ. The more preferred quantity of $BF_3$ used per mole of aromatic starting material is within the range of from about 1 to about 10 moles, with from about 3 to about 6 moles being most preferred.

Liquid $SO_2$ may be used as the sole solvent or it may be diluted with one or more additional solvents such as methylene dichloride, hydrogen fluoride, nitrobenzene, nitromethane, and similar materials which will dissolve the reactants. In the more preferred embodiment, anhydrous $SO_2$ is used as the sole solvent due to its inertness, low boiling point, ease of removal from the reaction medium and the fact that it has a beneficial influence on the percent conversion of the starting aromatic material and the selectivity towards production of the target aromatic ketone. Thus, in the preferred embodiment of this invention, the solvent consists essentially of liquid $SO_2$.

The reaction may be initiated by introducing the catalyst in gaseous or liquid form into a corrosion resistant reactor containing a cooled mixture of the aromatic reactant and the acylation agent dissolved in liquid $SO_2$. The reaction mass is then preferably maintained at a temperature of less than 0° C., more preferably less than about $-20°$ C., for a period of time ranging from about 1 to about 45 minutes. The reaction is then adjusted to a higher reaction temperature and for a specified reaction period. Reaction temperatures may vary within the range of from about −60 to about 50° C. and reaction times may vary from about one minute up to about 4 hours or more, depending upon the identity of the aromatic reactant, the acylating agent, the amount of catalyst employed, and the temperature at which the reaction is conducted. Higher catalyst concentrations within the above-described range cause the reaction to proceed more quickly and usually with more specificity with respect to yield of the target isomer ketone. The more preferred reaction temperatures generally range from about −40° C. to about +40° C., with −30° C. to about +20° C. being most preferred.

In the more preferred embodiment of the invention, the $BF_3$ catalyst is introduced into the reactor containing the other reactants maintained at a temperature below 0° C., more preferably below about −20° C. It has been found that with respect to reactions initiated at lower temperatures, i.e. about −20° C. or lower, the reaction proceeds faster and the yield of target isomer ketone, e.g. 4-isobutylacetophenone, is maximized. This result may be a consequence of the fact that the $BF_3$ gas is more soluble in liquids at lower temperatures and/or the fact that the $BF_3$ or $SO_2$ or $BF_3 \cdot SO_2$ complexes are less stable at higher temperatures. After a period of from about one to about 45 minutes at −20° C. or lower, the temperature of the reaction mass may then be adjusted to a temperature of up to about 50° C. which results in a concomitant pressure increase in the reactor of up to about 500 psig.

The catalyst and other materials may be charged to the reactor in any conventional form using technologies of handling well-known to those skilled in the art. In carrying out the reaction, an inert gas such as nitrogen may be used to keep the reaction space under the desired pressure, about 2.5 to about 500 psig, although this is often not necessary at higher reaction temperatures due to the vapor pressure exerted in the system by both $BF_3$ and $SO_2$.

In general, the process of this invention can result in the conversion of the starting aromatic reactant of at least about 90% under appropriate reaction conditions. For example, conversions in excess of 99% of 2-methyl naphthalene to the methylacetonaphthone derivative can be obtained. Where isobutylbenzene is the starting aromatic reactant, conversions in excess of 99% to isobutylacetophenone may be obtained, with a selectivity towards the desired 4-isobutylacetophenone isomer of greater than about 98%.

The following examples are illustrative of the invention.

EXAMPLE 1

This example illustrates the preparation of 4-isobutylacetophenone (4-IBAP) from isobutylbenzene (IBB) using acetic anhydride as the acetylating agent.

Isobutylbenzene (13.6 g, 0.101 mol), was added to a Hastelloy C autoclave which was then evacuated and cooled to a temperature of −40° C. Acetic anhydride (16.3 g, 0.160 mole) and anhydrous sulfur dioxide (156 g, 2.44 mol) were next added to the contents of the reactor. $BF_3$ gas (0.442 mol) was then admitted and the temperature of the reaction mass was slowly elevated to about 22° C. and maintained at that temperature for 120 minutes at a pressure of 100 psig. The relative molar ratio of IBB to acetic anhydride to $BF_3$ was approximately 1/1.6/4.4 respectively. Thereafter, the reactor was vented and the reaction solution was poured onto ice, neutralized to a pH of about 7.5 with ammonium hydroxide and then extracted with ethyl acetate. The ethyl acetate solution was dried over anhydrous magnesium sulfate and concentrated under reduced pressure to give a clear, pale yellow liquid crude product. The reaction proceeded with 99.7% conversion of IBB and with a selectivity towards the production of 4-IBAP of 98.7%, as determined by gas-liquid chromatography (GLC). The ratio of the production of the 3 isomer with respect to the 4 isomer was 0.0048.

EXAMPLE 2

The process of Example 1 was repeated except that the mole ratio of IBB to acetic anhydride to $BF_3$ was 1/1.5/4.3 respectively and the reaction temperature was elevated to 40° C. and held there for 30 minutes at a pressure of 160 psig. The conversion of IBB was determined by GLC to be 99.6% with a selectivity towards the 4-isobutylacetophenone isomer of 94.5%. The ratio of the production of the 3 isomer to the 4 isomer was 0.0026.

EXAMPLE 3

The process of Example 1 was repeated except that the $BF_3$ gas was introduced into the reactor at a temperature of −25° C. and the contents held there for a reaction period of 60 minutes.

The conversion of IBB was determined by GLC to be 99% with a selectivity towards the 4-isobutylacetophenone isomer of 99%. The ratio of the production of the 3 isomer to 4 isomer was 0.0041.

COMPARATIVE EXAMPLE A

This example illustrates the preparation of 4-IBAP by a prior art process using hydrogen fluoride (HF) as the sole catalyst and solvent.

Isobutylbenzene (254 g, 1.9 mol) and acetic anhydride (385 g, 3.8 mol) were added to a Hastelloy C autoclave which was then cooled to 5° C. and evacuated (150 mmHgA). Anhydrous hydrogen fluoride (1877 g, 94 mol) was added and the contents of the autoclave were warmed to 80° C. for 3 hours. The hydrogen fluoride was vented through a caustic scrubber using a nitrogen sparge. The contents of the autoclave were poured onto ice, neutralized to a pH of 7 with potassium hydroxide, and extracted with ethyl acetate. The ethyl acetate solution was dried over anhydrous magnesium sulfate and concentrated under reduced pressure to give the crude product. The reaction was determined by GLC to have proceeded with 85% conversion of isobutylbenzene and 81% selectivity to 4-IBAP.

Quite clearly the conversion of IBB and selectivity toward the production of 4-IBAP achieved by a process using HF as the sole catalyst is considerably less than that achieved using the process of the present invention.

COMPARATIVE EXAMPLE B

This example illustrates the preparation of 4-IBAP using a combination of $BF_3$ as a catalyst and HF as a solvent/co-catalyst.

Isobutylbenzene, acetic anhydride and hydrogen fluoride were combined in a reactor in a molar ratio of 1 to 2.0 to 52 respectively. The process as set forth in Example 1 was repeated except that 6.2 moles of $BF_3$ gas per mole of isobutylbenzene were admitted to the reactor and the reaction was conducted at a temperature of 40° C. for 120 minutes at a pressure of 67 psig. The reaction was found by GLC to have proceeded with a conversion if IBB in the range of 91 to 100% and a selectivity towards 4-IBAP of about 89.5%.

A comparison of the selectivity results achieved in Comparative Example B demonstrates that 4-IBAP selectivity is better using the combination of $BF_3$ and HF than using HF alone as in Comparative Example A, but inferior to the selectivity results achieved in Examples 1 through 3 wherein the $BF_3/SO_2$ catalyst and solvent combination were employed.

EXAMPLES 4-18

In the following examples, the acetylation process of Example 1 was carried out on different aromatic starting materials and under varied reaction conditions. In these examples, 2-methyl naphthalene (2 MEN) was acetylated to form 2,6-methyl acetonaphthone, 2-methoxy naphthalene (2-MON) was acetylated to form 2,6-methoxyacetophenone, biphenyl (BP) was acetylated to form 4'-phenyl acetophenone, biphenyl ether (BPE) was acetylated to produce either 4-monoacetyl biphenyl ether (MABPE) or 4,4'-diacetyl biphenyl ether (DABPE), depending on the molar ratio of acetylating agent, fluorobenzene (PhF) was acetylated to form p-fluoroacetophenone and isobutylbenzene was acetylated to form isobutylacetophenone. The molar ratio of acetylating agent to aromatic reactant used in these examples ranged from about 1 to about 3.5 moles of acetylating agent per mole of aromatic reactant, except in the case of Example 17 wherein the molar ratio of acetic anhydride to BPE was 1 to 0.46 and in the case of Example 18 wherein this molar ratio was 1 to 0.77.

The identity of the reactants and reaction conditions are as set forth in Table 1. The catalyst employed in each example was $BF_3$ and the solvent was $SO_2$. Conversions of the starting aromatic compounds and selectivities towards the target isomers are listed in the last columns of the table.

TABLE I

| EXAMPLE | CEL # | AROMATIC | ACET. AGENT | MOLE RATIO $BF_3$/ AROMATIC | MOLE RATIO ACETYLATING AGENT/ AROMATIC | TEMP. (°C.) | TIME MIN. | PRESSURE (PSIG) | CONVERSION | SELECTIVITY TO DESIRED ISOMER (%) |
|---|---|---|---|---|---|---|---|---|---|---|
| 4 | 71901 | 2 MEN | AcF* | 2.5 | 1.5 | 23 | 120 | 55 | 100% | 86 |
| 5 | 71903 | 2 MEN | AcF | 3.0 | 1.8 | 0 | 120 | 39 | 100% | 89 |
| 6 | 71905 | 2 MEN | AcF | 1.2 | 1.4 | 0 | 120 | 23 | 100% | 81 |
| 7 | 71907 | 2 MEN | AcF | 1.2 | 1.6 | 20 | 120 | 50 | 100% | 88 |
| 8 | 71921 | 2 MEN | $Ac_2O$* | 6.4 | 1.6 | 24 | 120 | 180 | 100% | 82 |
| 9 | 71929 | BP | AcF | 3.1 | 3.5 | 24 | 120 | 87 | 100% | 99 |
| 10 | 71937 | PhF | AcF | 2.9 | 1.6 | 25 | 120 | 105 | 70% | 98 |
| 11 | 71941 | 2 MEN | $Ac_2O$ | 5.5 | 1.5 | 40 | 120 | 230 | 100% | 83 |
| 12 | 76906 | 2 MEN | AcF | 9.2 | 1.9 | −10 | 120 | 150 | 100% | 74 |
| 13 | 76912 | 2 MEN | AcF | 9.0 | 1.7 | −44 | 120 | 66 | 100% | 71 |
| 14 | 76927 | 2 MON | $Ac_2O$ | 10.0 | 1.5 | 40 | 60 | 365 | 100% | — |
| 15 | 76918 | IBB | AcCl* | 5.9 | 1.6 | 20 | 110 | 250 | 63% | 98 |
| 16 | 848-22 | BPE | $Ac_2O$ | 9.0 | 1.6 | 23 | 120 | 295 | 100% | 99.8 (DABPE) |
| 17 | 885-19 | BPE | $Ac_2O$ | 9.4 | 0.46 | 22 | 60 | 505 | 86%** | 99 (MABPE) |
| 18 | 801-22 | BPE | $Ac_2O$ | 9.6 | 0.77 | 25 | 120 | 340 | 99.6%** | 49.6 (MABPE) 50.4 (DABPE) |

Notes:
*AcF - Acetyl Fluoride; $AC_2O$ - Acetic Anhydride; AcCl - Acetyl Chloride
**All Ac groups reacted

What is claimed is:

1. A process for selectively preparing 4-isobutylacetophenone from isobutylbenzene in which at least about 95% of said isobutylbenzene is converted to 4-isobutylacetophenone, said process comprising acetylating isobutylbenzene with an acetylating agent selected from the group consisting of acetic acid, acetic anhydride, acetyl fluoride, acetyl chloride, and acetyl bromide in the presence of a solvent comprising anhydrous sulfur dioxide and catalytic quantities of $BF_3$, said acetylation being accomplished at a temperature that is initially maintained at no more than about −20° C. for at least one minute and is then increased to no more than 50° C. until said acetylation is completed.

2. The process of claim 1 wherein said $BF_3$ is present at a ratio of from about 1 to about 15 moles per mole of isobutylbenzene.

3. The process of claim 2 wherein said $BF_3$ is present at a ratio of from about 3 to about 6 moles per mole of isobutylbenzene.

4. The process of claim 2 wherein said acetylating agent is present at a ratio of from about 0.5 to about 4 moles per mole of isobutylbenzene.

5. The process of claim 4 wherein said acetylating agent is present at a ratio of from about 1 to about 3 moles per mole of isobutylbenzene.

6. The process of claim 5 which is conducted at a temperature within the range of from about −60° C. to about +50° C.

7. The process of claim 6 wherein said temperature is within the range of from about −40° C. to about +20° C.

8. The process of claim 6 wherein said temperature is in the range of from about +30° C. to about +50° C.

9. The process of claim 6 wherein said acetylating agent is acetic anhydride.

10. The process of claim 6 wherein said solvent consists essentially of anhydrous sulfur dioxide and is present at a ratio of from about 5 to about 75 moles per mole of isobutylbenzene.

11. The process of claim 6 wherein said $BF_3$ is present at a ratio of from about 3 to about 6 moles per mole of isobutylbenzene and wherein said acetylation reaction is conducted at a temperature of from about −40° C. to about +20° C.

* * * * *